(12) United States Patent
Parker et al.

(10) Patent No.: US 7,546,747 B2
(45) Date of Patent: Jun. 16, 2009

(54) PROCESS FOR PRODUCTION OF A DRIED CARBOXYLIC ACID CAKE SUITABLE FOR USE IN POLYESTER PRODUCTION

(75) Inventors: Kenny Randolph Parker, Afton, TN (US); Robert Lin, Kingsport, TN (US); Philip Edward Gibson, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 221 days.

(21) Appl. No.: 10/758,676

(22) Filed: Jan. 15, 2004

(65) Prior Publication Data

US 2005/0159616 A1  Jul. 21, 2005

(51) Int. Cl.
*C07C 51/42* (2006.01)
*C07C 51/16* (2006.01)

(52) U.S. Cl. .......................... 62/486; 562/416
(58) Field of Classification Search ................. 562/416, 562/486
See application file for complete search history.

(56) References Cited

U.S. PATENT DOCUMENTS

| | | | |
|---|---|---|---|
| 3,057,909 A | 10/1962 | Sebelist et al. | |
| 3,064,044 A | 11/1962 | Baldwin | |
| 3,170,768 A | 2/1965 | Baldwin | |
| 3,513,193 A * | 5/1970 | Katzschmann | 562/485 |
| 3,584,039 A | 6/1971 | Meyer | |
| 3,683,018 A | 8/1972 | Longland, Jr. | |
| 3,839,436 A | 10/1974 | Longland, Jr. | |
| 3,850,983 A | 11/1974 | Park | |
| 3,931,305 A | 1/1976 | Fisher | |
| 4,158,738 A * | 6/1979 | Scott et al. | 562/416 |
| 4,201,871 A | 5/1980 | Tanouchi et al. | |
| 4,268,690 A | 5/1981 | Komatsu et al. | |
| 4,314,073 A | 2/1982 | Crooks | |
| 4,330,676 A | 5/1982 | Moxham | |
| 4,334,086 A | 6/1982 | Hanotier et al. | |
| 4,356,319 A | 10/1982 | Roffia et al. | |
| 4,357,475 A | 11/1982 | Hanotier et al. | |
| 4,447,646 A | 5/1984 | Johnson et al. | |
| 4,500,732 A | 2/1985 | Petty-Weeks et al. | |

(Continued)

FOREIGN PATENT DOCUMENTS

DE  31 28 474 A1  6/1982

(Continued)

OTHER PUBLICATIONS

Copending U.S. Appl. No. 11/346,393, filed Feb. 2, 2006.

(Continued)

*Primary Examiner*—Taylor Victor Oh
(74) *Attorney, Agent, or Firm*—Steven A. Owen; Bernard J. Graves, Jr.

(57) ABSTRACT

The present invention relates to a process by which a dried carboxylic acid cake is obtained from a slurry or cake carboxylic acid product through the use of at least one counter current wash. More specifically, the present invention relates to a process by which a dried terephthalic acid cake suitable as a starting material for polyester or co-polyester production is obtained from a slurry or cake terephthalic acid product through the use of at least one counter current wash.

22 Claims, 2 Drawing Sheets

U.S. PATENT DOCUMENTS

| | | | |
|---|---|---|---|
| 4,605,763 | A | 8/1986 | Kiefer et al. |
| 4,939,297 | A | 7/1990 | Browder et al. |
| 5,008,450 | A | 4/1991 | Yamamoto et al. |
| 5,095,146 | A | 3/1992 | Zeitlin et al. |
| 5,175,355 | A | 12/1992 | Streich et al. |
| 5,200,557 | A * | 4/1993 | Gee et al. .................. 562/486 |
| 5,359,133 | A | 10/1994 | Nazimok et al. |
| 5,563,293 | A | 10/1996 | Hindmarsh et al. |
| 5,567,842 | A | 10/1996 | Izumisawa et al. |
| 5,583,254 | A | 12/1996 | Turner et al. |
| 5,684,187 | A | 11/1997 | Ohkoshi et al. |
| 5,712,412 | A | 1/1998 | Inary et al. |
| 5,777,161 | A | 7/1998 | Inary |
| 6,013,835 | A * | 1/2000 | Lee et al. .................. 562/487 |
| 6,297,348 | B1 | 10/2001 | Rodden et al. |
| 6,307,099 | B1 | 10/2001 | Turner et al. |
| 2002/0183546 | A1 | 12/2002 | Sheppard et al. |
| 2004/0215036 | A1 | 10/2004 | Lin et al. |

FOREIGN PATENT DOCUMENTS

| | | |
|---|---|---|
| GB | 1152577 | 5/1969 |
| GB | 1260755 | 1/1972 |
| GB | 1388289 | 3/1975 |
| JP | 48-26740 A | 9/1973 |
| JP | 7-149690 A | 6/1995 |
| JP | 7-291896 A | 11/1995 |
| JP | 9-286758 A | 11/1997 |
| JP | 9-286759 A | 11/1997 |
| JP | 2002-230819 A | 8/2002 |
| JP | 2003-128624 A | 5/2003 |
| WO | WO 93/24440 A1 | 12/1993 |
| WO | WO 94/17892 A1 | 8/1994 |
| WO | WO 98/38150 A1 | 9/1998 |
| WO | WO 2004/052820 A1 | 6/2004 |
| WO | WO 2006/125144 A1 | 11/2006 |

OTHER PUBLICATIONS

USPTO Office Action dated Oct. 4, 2005 for U.S. Appl. No. 10/667,744.

USPTO Office Action dated Jul. 12, 2005 for U.S. Appl. No. 10/667,744.

USPTO Office Action dated Nov. 29, 2004 for U.S. Appl. No. 10/667,744.

Copending—U.S. Appl. No. 10/645,737, filed Aug. 21, 2003 by Sheppard et al.

Copending—U.S. Appl. No. 10/667,744, filed Sep. 22, 2003 by Jenkins, Jr. et al.

Copending—U.S. Appl. No. 10/645,734, filed Aug. 21, 2003 by Sheppard et al.

Copending—U.S. Appl. No. 10/872,248, filed Jun. 18, 2004 by Sheppard.

U.S. Appl. No. 10/271,058, filed Oct. 15, 2002, Lin et al.

U.S. Appl. No. 10/383,126, filed Mar. 6, 2003, Lin.

Arun Pal Aneja and Viney Pal Aneja, "The Effect of Water and Air Contamination on Poly (Ethylene Terephthalate) Formation", *Polymer Engineering Reviews*, 1982, pp. 123-133, vol. 2, No. 2.

M. Maties, R. Bacai Oglu, R.F. Paie & H.H. Glatt, "Study of Di- and Polyesterification, I. Esterification of Ethylene and Diethylene Glycols with Acetic Acid", (1978), Chemical Bulletin of the Technical University of Timisoara, 23(37), pp. 73-76.

USPTO Office Action dated Nov. 30, 2004 for U.S. Appl. No. 10/645,734.

USPTO Office Action dated Apr. 21, 2004 for U.S. Appl. No. 10/645,734.

USPTO Office Action dated Apr. 22, 2003 for U.S. Appl. No. 10/315,294.

USPTO Office Action dated Dec. 10, 2004 for U.S. Appl. No. 10/645,737.

USPTO Office Action dated Apr. 19, 2004 for U.S. Appl. No. 10/645,737.

USPTO office action dated Aug. 24, 2006 for copending U.S. Appl. No. 10/872,248.

Co-pending U.S. Appl. No. 11/654,468, filed Jan. 17, 2007, Ruairi Seosamh O'Meadhra et al.

USPTO Office Action dated Jun. 4, 2007 for copending U.S. Appl. No. 11/346,393.

USPTO Office Action dated Jul. 13, 2007 for co-pending U.S. Appl. No. 10/872,248.

USPTO Office Action dated Sep. 21, 2007 for copending U.S. Appl. No. 10/872,248.

USPTO Office Action dated Apr. 15, 2008 for copending U.S. Appl. No. 11/654,468.

* cited by examiner

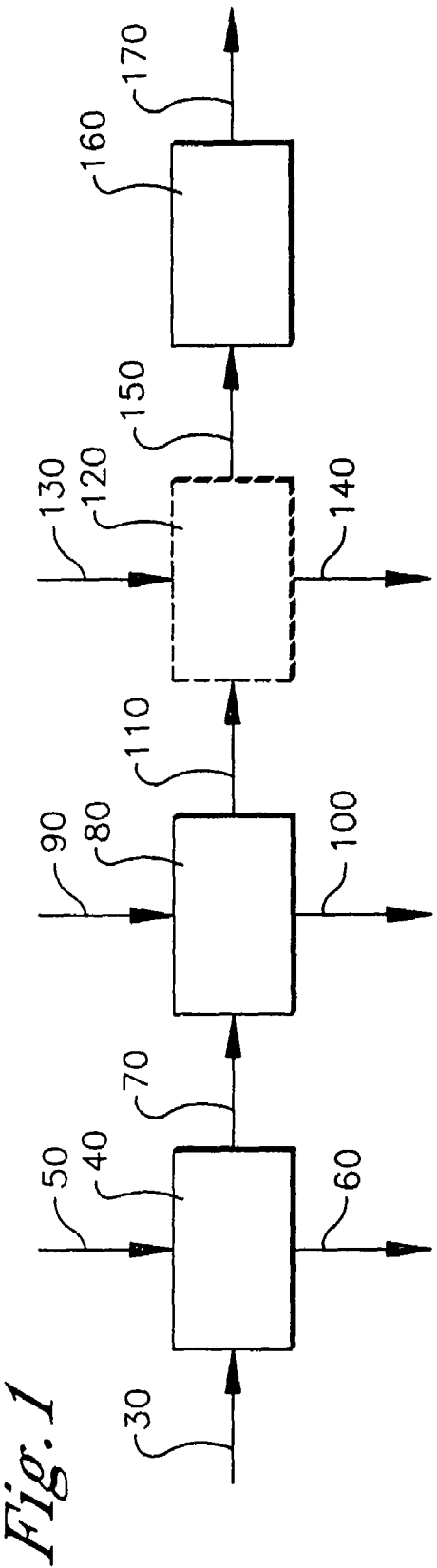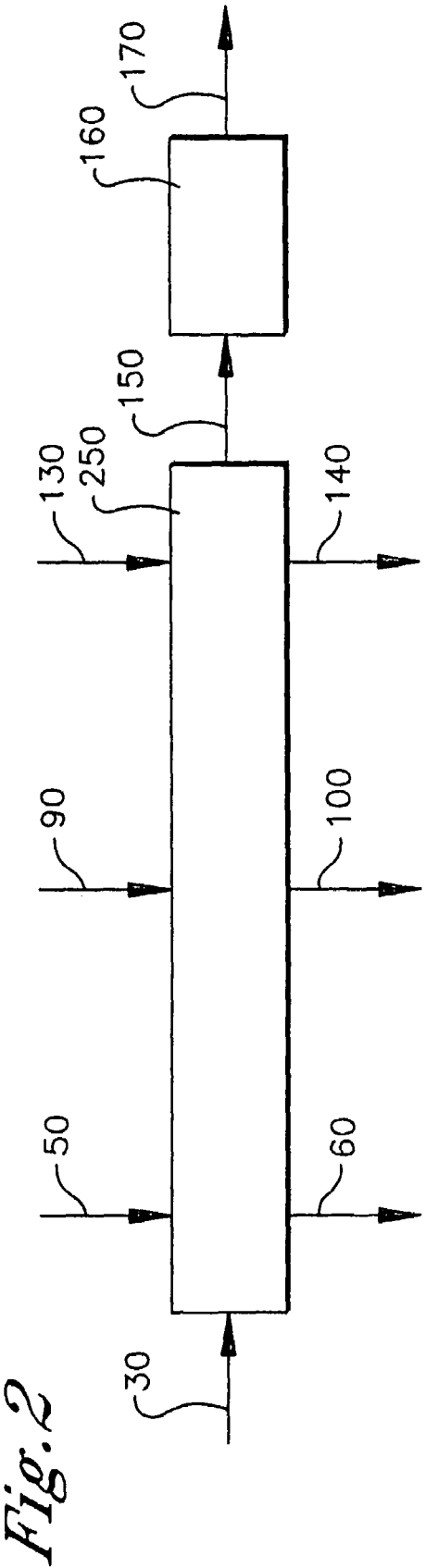

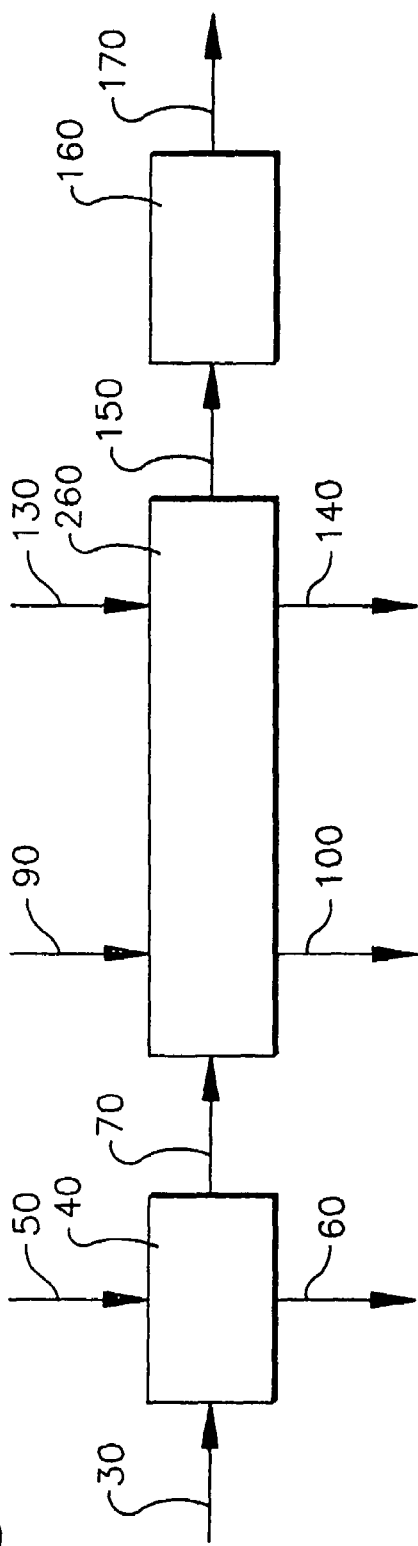
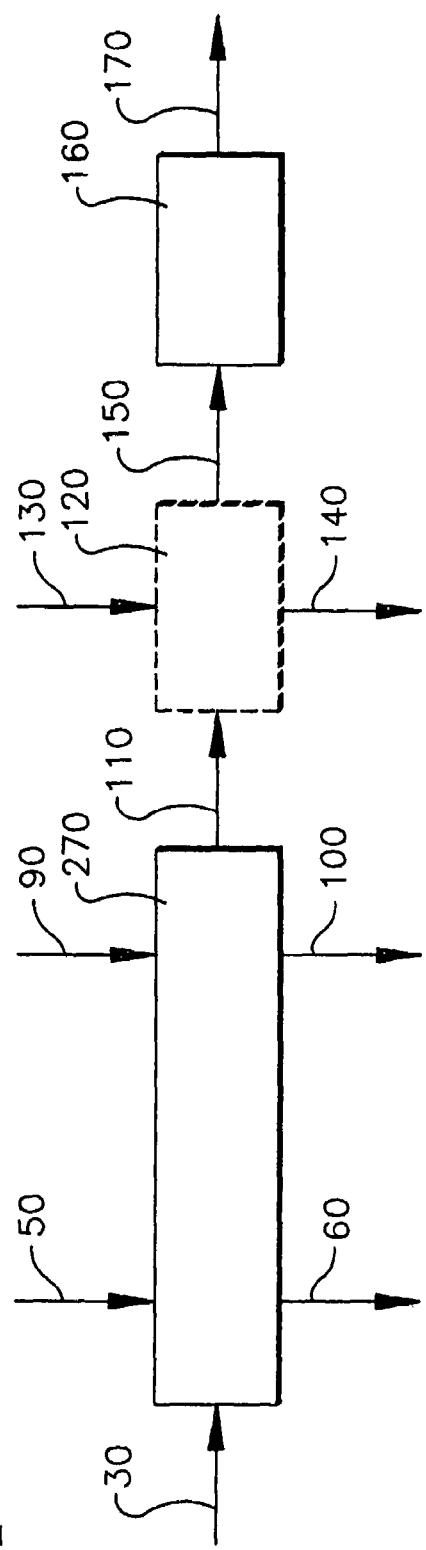

PROCESS FOR PRODUCTION OF A DRIED CARBOXYLIC ACID CAKE SUITABLE FOR USE IN POLYESTER PRODUCTION

FIELD OF INVENTION

The present invention relates to a process by which a dried carboxylic acid cake is obtained from a slurry or cake carboxylic acid product through the use of at least one counter current wash. More specifically, the present invention relates to a process by which a dried terephthalic acid cake suitable as a starting material for polyester or co-polyester production is obtained from a slurry or cake terephthalic acid product through the use of at least one counter current wash.

BACKGROUND OF THE INVENTION

Pursuant to the goal of making polyethylene terephthalate (PET) and other polyesters or co-polyesters, a great deal of patent literature is dedicated to describing the processes for preparing a dried carboxylic acid cake suitable as starting material. In general, these inventions describe specific mixing schemes with a purified terephthalic acid solid and liquid ethylene glycol. Additionally, there is substantial body of literature devoted to producing a purified terephthalic acid in the powder form that is suitable for use in producing PET and other polyesters or co-polyesters.

The objective of this invention is to describe a process by which the dried carboxylic acid cake suitable as a starting material for polyester or co-polyester production is obtained from a slurry or cake carboxylic acid product through the use of a counter current solvent wash zone. More specifically, the objective of this invention is to describe a process by which a dried terephthalic acid cake suitable as a starting material for polyester or co-polyester production is obtained from a slurry or cake terephthalic acid product through the use of a counter current solvent wash zone to reduce the amount of fresh solvent used in the process.

Usually, purified terephthalic acid solid is produced in a multi-step process wherein a crude terephthalic acid is produced. Liquid phase oxidation of p-xylene produces crude terephthalic acid. The crude terephthalic acid does not have sufficient quality for direct use as starting material in commercial PET. Instead, the crude terephthalic acid is usually refined to purified terephthalic acid solid.

Usually in terephthalic acid purification processes, the crude terephthalic acid is dissolved in water and hydrogenated for the purpose of converting 4-carboxybenzaldehyde to p-toluic acid, which is a more water-soluble derivative, and for the purpose of converting characteristically yellow compounds to colorless derivatives. Significant 4-carboxybenzaldehyde or p-toluic acid in the final purified terephthalic acid product is particularly detrimental to polymerization processes as each can act as a chain terminator during the condensation reaction between terephthalic acid and ethylene glycol in the production of PET. Typical purified terephthalic acid contains on a weight basis less than 25 parts per million (ppm) 4-carboxybenzaldehyde and less than 150 ppm p-toluic acid.

A number of other processes have been developed where a terephthalic acid suitable as starting material for commercial PET production without the use of hydrogenation. Typically, terephthalic acid production processes involve catalyzed oxidation of p-xylene in an acetic acid solvent followed by filtration and drying of the terephthalic acid.

Typically, terephthalic acid (TPA) produced via catalyzed oxidation of p-xylene in an acetic acid solvent produces a slurry or cake terephthalic acid product that contains residual catalyst (e.g cobalt, manganese, and bromine compounds). In a common method of producing a substantially dry TPA solid from a slurry or cake terephthalic acid product, the slurry or cake terephthalic acid product is filtered to separate a substantial amount of the acetic acid liquid from the TPA solids. Residual catalyst is usually separated from the slurry or cake terephthalic acid product by washing (rinsing) the wet cake with catalyst-free acetic acid, water or other solvent. The TPA solid is isolated by drying.

In the present invention, a novel process has been discovered resulting in less solvent used than currently employed processes. In the conventional approach toward producing terephthalic acid via catalyzed oxidation of p-xylene in an acetic acid solvent, a slurry or cake terephthalic acid product is filtered, washed, then dried to produce a terephthalic acid powder suitable as starting material for PET production.

In one embodiment of the present invention, the slurry or cake terephthalic acid product is filtered to produce a terephthalic acid cake with solvent and a TPA solvent mother liquor stream. The terephthalic acid cake with solvent is then washed (rinsed) with water to recover residual metal catalyst material and to produce a water-wet terephthalic acid cake and an TPA solvent/water by-product liquor. The water-wet terephthalic acid cake is then dried to produce a dried terephthalic acid cake suitable as starting material in a commercial PET process. In this embodiment of the invention at least one counter current wash is utilized. By utilizing a counter current solvent wash zone the amount of solvent used can be reduced substantially as compared to a process without counter current washing. In addition, by utilizing at least one counter current wash may result in reduction of equipment size and energy as compare to a TPA production process without a counter current wash.

SUMMARY OF THE INVENTION

The present invention relates to a process by which a dried carboxylic acid cake is obtained from a slurry or cake carboxylic acid product. More specifically, the present invention relates to a process for the production of a dried terephthalic acid cake suitable as feedstock for the production of commercial PET. The resulting process utilizes less solvent than currently employed processes that do not utilize a counter current solvent wash zone.

It is an object of this invention to provide a process for producing a dried carboxylic acid cake from a slurry or cake carboxylic acid product though the use of at least one counter current wash.

It is another object of this invention to provide a process for producing a dried terephthalic acid cake from a slurry or cake terephthalic acid product.

It is another object of this invention to provide a process for producing a dried terephthalic acid cake from a terephthalic acid solvent slurry or cake through the use of a counter current solvent wash zone.

In a first embodiment of this invention, a process for producing a dried carboxylic acid cake is provided, the process comprises:

(a) removing in a liquor exchange zone impurities from a carboxylic acid slurry to form a water-wet carboxylic acid cake, a mother liquor stream, a solvent mother liquor stream, and a solvent/water byproduct liquor stream; wherein solvent or water is added counter current to the flow of the carboxylic acid slurry;

(b) drying the water-wet carboxylic acid cake in a drying zone to form the dried carboxylic acid cake.

In another embodiment of this invention, a process for producing a dried carboxylic acid cake is provided, the process comprises:

(a) removing in a solvent liquor exchange zone impurities from a carboxylic acid slurry to form a carboxylic acid cake with solvent, a mother liquor stream, and a solvent mother liquor stream;

(b) adding water in a counter current water wash zone to the carboxylic cake with solvent to produce a water-wet carboxylic acid cake and a solvent/water by product liquor stream;

(c) drying the water-wet carboxylic acid cake in a drying zone to form the dried carboxylic acid cake.

In another embodiment of this invention, a process for producing a dried carboxylic acid cake is provided, the process comprises:

(a) removing in a solid-liquid separation zone impurities from a carboxylic acid slurry to form a slurry or cake product and a mother liquor stream;

(b) removing in a counter current solvent-water liquor exchange zone residual impurities from the slurry or cake product to form a water-wet carboxylic acid cake, a solvent mother liquor stream, and a solvent/water byproduct liquor stream; and (c) drying the water-wet carboxylic acid cake in a drying zone to form the dried carboxylic acid cake.

In another embodiment of this invention, a process for producing a dried carboxylic acid cake is provided, the process comprises:

(a) removing a solvent from a slurry or cake product in a counter current solvent-water liquor exchange zone; wherein a substantial portion of the solvent in the slurry or cake product is replaced with water to form a water-wet carboxylic acid cake;

(b) drying the water-wet carboxylic acid cake in a drying zone to form the dried carboxylic acid cake.

In another embodiment of this invention, a process for producing a dried terephthalic acid cake is provided, the process comprises:

(a) removing in a counter current solvent wash zone residual impurities from a slurry or cake terephthalic acid product to form a terephthalic acid cake with acetic acid;

(b) removing a substantial portion of a solvent in a counter current water wash zone from the terephthalic acid cake with acetic acid to form a water-wet terephthalic acid cake; and (c) drying the water-wet carboxylic acid cake in a drying zone to form the dried carboxylic acid cake.

In another embodiment of this invention, a process for producing a dried terephthalic acid cake is provided, the process comprises:

(a) removing a solvent from a slurry or cake terephthalic acid product in a counter current solvent-water liquor exchange zone; wherein a substantial portion of the solvent in the slurry or cake terephthalic acid product is replaced with water to form a water-wet terephthalic acid cake;

(b) drying the water-wet terephthalic acid cake in a drying zone to form the dried terephthalic acid cake.

In another embodiment of this invention, a process for producing a dried terephthalic acid cake is provided, the process comprises:

(a) removing in a counter current solvent wash zone residual impurities from a slurry or cake terephthalic acid product from a terephthalic acid cake with acetic acid; wherein the counter current wash zone comprises at least one solid-liquid separation device that is operated at a temperature between about 40° C. to about 155° C.;

(b) removing a substantial portion of a solvent in a counter current water wash zone from the terephthalic acid cake with acetic acid to form a water-wet terephthalic acid cake; wherein the counter current water wash zone comprises at least one solid-liquid separation device that is operated at a temperature between about 40° C. to about 155° C.;

(c) drying the water-wet terephthalic acid cake in a drying zone to form the dried terephthalic acid cake.

In another embodiment of this invention, a process for producing a dried carboxylic acid cake is provided, the process comprises:

(a) removing in a solid-liquid separation zone impurities from a carboxylic acid slurry to form a slurry or cake product and a mother liquor stream;

(b) adding solvent to a slurry or cake product in a counter current solvent wash zone to the slurry or cake product to produce a carboxylic acid cake with solvent and a solvent mother liquor stream;

(c) optionally adding water in a counter current water wash zone to the carboxylic cake with solvent to produce a water-wet carboxylic acid cake and a solvent/water by product liquor stream;

(d) drying the water-wet carboxylic acid cake in a drying zone to form the dried carboxylic acid cake.

In another embodiment of this invention, a process for producing a dried terephthalic acid cake is provided, the process comprises:

(a) removing in a solid-liquid separation zone impurities from a terephthalic acid slurry to form a slurry or cake terephthalic acid product and a mother liquor stream;

(b) adding solvent in a counter current solvent wash zone to the slurry or cake terephthalic acid product to produce a terephthalic acid cake with solvent and a solvent mother liquor stream;

(c) optionally, adding water in a counter current water wash zone to the terephthalic acid cake with solvent to produce a water-wet terephthalic acid cake and a solvent/water by product liquor stream;

(d) drying the water-wet carboxylic acid cake in a drying zone to form the dried carboxylic acid cake.

These objects, and other objects, will become more apparent to others with ordinary skill in the art after reading this disclosure.

BRIEF DESCRIPTION OF THE DRAWINGS

FIG. 1 illustrates one embodiment of this invention, a process for producing a dried carboxylic acid cake.

FIG. 2 illustrates another embodiment of this invention, a process for producing a dried carboxylic acid cake by utilizing a liquor exchange zone.

FIG. 3 illustrates another embodiment of this invention, a process for producing a dried carboxylic acid cake by utilizing a counter current solvent-water liquor exchange zone.

FIG. 4 illustrates another embodiment of this invention, a process for producing a dried carboxylic acid cake by utilizing a solvent liquor exchange zone.

DESCRIPTION OF THE INVENTION

In an embodiment of this invention shown in FIG. 1, a process for producing a dried carboxylic acid cake 170 is provided. The process comprises:

Step (a) comprises optionally removing impurities from a carboxylic acid slurry 30 in an solid-liquid displacement zone 40 to form a slurry or cake carboxylic acid product 70 and a mother liquor stream 60;

A carboxylic acid slurry comprises at least one carboxylic acid, catalyst, at least one solvent, and impurities is introduced via lines not shown. The impurities typically comprise at least one or more of the following compounds: 4-carboxybenzaldehyde (4-CBA), trimellitic acid (TMA), and 2,6-dicarboxyfluorenone (2,6-DCF). Suitable solvents include, but are not limited to, aliphatic mono-carboxylic acids, preferably containing 2 to 6 carbon atoms, or benzoic acid and mixtures thereof and mixtures of these compounds with water. Preferably the solvent is acetic acid mixed with water, in a ratio of about 5:1 to about 99:1, preferably between about 8:1 and about 49:1. Throughout the specification acetic acid will be referred to as the solvent. However, it should be appreciated that other suitable solvents, such as those disclosed previously, may also be utilized. The solvent typically comprises acetic acid, but can be any solvent that has been previously mentioned.

The carboxylic acid slurry can be produced by oxidizing in a oxidation zone an aromatic feed stock. In one embodiment, the aromatic feedstock comprises paraxylene. The oxidation zone comprises at least one oxidation reactor, and the carboxylic acid slurry comprises at least one carboxylic acid. The oxidation reactor can be operated at temperatures between about 120° C. and about 250° C., preferably about 140° C. to about 170° C. Typically the aromatic feed stock comprises paraxylene and the carboxylic acid comprises terephthalic acid. In one embodiment of the invention the oxidation zone comprises a bubble column.

Therefore, for example, when terephthalic acid is utilized, the carboxylic acid slurry 30 would be referred to as terephthalic acid slurry and the dried carboxylic acid cake 170 would be referred to as a dried terephthalic acid cake.

Carboxylic acids include any carboxylic acid produced via controlled oxidation of an organic precursor compound. For example, carboxylic acids include aromatic dicarboxylic acids preferably having 8 to 14 carbon atoms, aliphatic dicarboxylic acids preferably having 4 to 12 carbon atoms, or cycloaliphatic dicarboxylic acids preferably having 8 to 12 carbon atoms. Other examples of suitable carboxylic acids include, but are not limited to, terephthalic acid, benzoic, p-toulic, isophthalic acid, trimellitic acid, naphthalene dicarboxylic acid, cyclohexanedicarboxylic acid, cyclohexanediacetic acid, diphenyl-4,4'-dicarboxylic acid, diphenyl-3,4'-dicarboxylic acid, 2,2,-dimethyl-1,3-propandiol dicarboxylic acid, succinic acid, glutaric acid, adipic acid, azelaic acid, sebacic acid, and mixtures thereof.

Terephthalic acid slurry is conventionally synthesized via the liquid phase oxidation of paraxylene in the presence of suitable oxidation catalyst. Suitable catalysts include, but are not limited to, cobalt, manganese and bromine compounds, which are soluble in the selected solvent. In one embodiment of the invention the catalyst comprises cobalt, bromine and manganese. The cobalt and manganese combined can be in concentrations of about 100 ppm to about 2700 ppm by weight in the liquor. The bromine can be in concentrations of about 1000 ppm to about 2500 ppm by weight in the liquor.

The carboxylic acid slurry is fed to a solid-liquid displacement zone 40 capable of removing a portion of the liquid contained in the carboxylic acid slurry 30 to produce a slurry or cake carboxylic acid product in conduit 70. The removal of a portion of the liquid to produce a slurry or cake carboxylic acid product in conduit 70 can be accomplished by any means known in the art. A portion means at least 5% by weight of the liquid is removed. Typically, the solid-liquid displacement zone 40 comprises a solid-liquid separator that is selected from the group consisting of a decanter centrifuge, rotary disk centrifuge, belt filter, rotary vacuum filter, and the like. The carboxylic acid slurry in conduit 30 is fed to the solid-liquid displacement zone 40 comprising at least one solid-liquid separator. The solid-liquid separator(s) can be operated at temperatures between about 50° C. to about 200° C., preferably 140° C. to about 170° C. The solid-liquid separator(s) can be operated at pressures between about 0 psig to about 200 psig. The solid-liquid separator in the solid-liquid displacement zone 40 may be operated in continuous or batch mode, although it will be appreciated that for commercial processes, the continuous mode is preferred.

The impurities are displaced from the solid-liquid displacement zone 40 into a mother liquor stream and withdrawn via line 60. In one embodiment of the invention, additional solvent is fed to the solid-liquid displacement zone 40 via line 50 to reslurry the carboxylic acid slurry 30 and form a slurry or cake carboxylic acid product 70. When a terephthalic acid slurry is utilized in the solid-liquid separation zone 40, a slurry or cake terephthalic acid product is produced. The slurry or cake terephthalic acid product typically comprises terephthalic acid and acetic acid. The mother liquor 60 is withdrawn from solid-liquid displacement zone 40 via line 60 and comprises a solvent, typically acetic acid, catalyst, and bromine compounds. The mother liquor in line 60 may either be sent to a process for separating impurities from oxidation solvent via lines not shown or recycled to the catalyst system via lines not shown. One technique for impurity removal from the mother liquor 60 commonly used in the chemical processing industry is to draw out or "purge" some portion of the recycle stream. Typically, the purge stream is simply disposed of or, if economically justified, subjected to various treatments to remove undesired impurities while recovering valuable components. Examples of impurity removal processes include U.S. Pat. No. 4,939,297 and U.S. Pat. No. 4,356,319, herein incorporated by reference.

Step (b) comprises removing in a counter current solvent wash zone 80 residual impurities from a slurry or cake carboxylic acid product 70 to form a carboxylic acid cake with solvent 110 and a solvent mother liquor stream 100.

Conduit 70 contains a slurry or cake carboxylic acid product 70 comprising a carboxylic acid, residual impurities and a solvent. The residual impurities comprise residual catalyst (typically but not limited to cobalt, manganese, or bromine). Suitable solvents include, but are not limited to, aliphatic mono-carboxylic acids, preferably containing 2 to 6 carbon atoms, or benzoic acid and mixtures thereof and mixtures of these compounds with water. Preferably, the solvent is comprised of mainly acetic acid and/or some water. The ratio of acetic acid to water can range from 50:50 to 99:1 acetic acid to water by mass, more preferably in the range of 85:15 to 98:2, and most preferably in the range of 90:10 to 97:3. Suitable carboxylic acids include by are not limited to terephthalic acid, isophthalic acid, naphthalene dicarboxylic acid, trimellitic acid, and mixtures thereof.

The slurry or cake carboxylic acid product 70 is in the range of 10-90% by weight carboxylic acid. Preferably the slurry or cake carboxylic acid product 70 is in the range of 25-40% by weight carboxylic acid for a slurry and in the range of 70-90% by weight for the cake product. Most preferably, the slurry or cake carboxylic acid product 70 is in the range of 30-40% by weight carboxylic acid. The slurry or cake carboxylic acid product in conduit 70 is then introduced into a counter current solvent wash zone 80, wherein a substantial portion of solvent is recovered in the solvent mother liquor stream in conduit 100. The solvent mother liquor 102 comprises a substantial portion of the solvent. Additional solvent can be added via conduit 90 counter current to the flow of the slurry or cake carboxylic acid product 70 in the counter current solvent wash zone 80. The amount of stages of counter current wash can be any amount of stages necessary to produce the carboxylic cake with solvent to the desired purity. Typically, the amount of stages in the counter current wash can be about 1 to about 8, preferably about 2 to about 6, most preferably about 2 to about 4. For wash with more than one stage, counter current flow is preferable.

The counter current solvent wash zone 80 comprises at least one solid-liquid separation device capable of efficiently separating solids and liquids. The solid-liquid separation device can typically be comprised of, but not limited to, the following types of devices: centrifuges, cyclones, rotary drum filters, belt filters, press filters, etc. The counter current solvent wash zone 80 comprises at least one solid-liquid separation device(s) 110 which can operate within a temperature range of from approximately 40° C. to 155° C. Preferably the solid-liquid separation device(s) 110 can operate within a temperature range of from about 80° C. to about 150° C. Most preferably the solid-liquid separation device(s) 110 can operate within a temperature range of from about 90° C. to about 150° C. A carboxylic acid cake with solvent 110, is produced wherein the moisture composition of the carboxylic acid cake with solvent 110 can be in the range of 0.5-30% by weight moisture, preferably in the range of 1-20% moisture, most preferably in the range of 1-10% moisture. Optionally, the residual solvent can be removed by a gas displacement step to minimize solvent contamination with wash. When the carboxylic acid is terephthalic acid and the solvent is acetic acid a terephthalic acid cake with acetic acid is produced.

Step (c) comprises optionally removing a substantial portion of a solvent in a counter current water wash zone 120 from the carboxylic acid cake with solvent 110 to form a water-wet carboxylic acid cake 100 and a solvent/water byproduct liquor stream 140.

The carboxylic acid cake with solvent 110, is then subjected to a wash or "rinsing" with water or substantially water with residual amounts of solvent in the counter current water wash zone 120, wherein a substantial portion of the solvent is replaced with water to form a water-wet carboxylic acid cake 150. The water-wet carboxylic acid cake 150, is preferably in the range of about 0.5% to about 30% moisture, more preferably in the range of about 1 to about 20% moisture, and most preferably in the range of about 1% to about 10% moisture. The residual moisture of the water-wet carboxylic acid cake 150, should contain less than about 2% solvent on a mass basis. Additionally, the water-wet carboxylic acid cake 150 should contain less than 1% of any metals, preferably less than 100 ppm by weight, most preferably less than 10 ppm by weight, typically used as catalysts in p-xylene oxidation, in the slurry or cake carboxylic acid product in conduit 70, should remain in the water-wet carboxylic acid cake 150. Examples of metals include but are not limited to cobalt, and manganese.

Wash water is introduced into the counter current water wash zone 120 via conduit 130. The wash water should be, on a continuous basis, comprise a mass feed rate in ratio with the solids in the carboxylic cake with solvent 110 in the range of about 0.1:1 to about 1.5:1, preferably in the range of about 0.1:1 to about 0.6:1, most preferably in the range of about 0.2:1 to about 0.4:1. There are no limitations on the temperature or pressure of the wash water including the use of vaporized water, steam, or a combination of water and steam, as wash. In one embodiment of the invention, wash water is introduced counter current to the carboxylic acid cake with solvent.

Additional wash water can be added via conduit 130 counter current to the flow of the carboxylic acid cake with solvent 110 in the counter current water wash zone 120. The amount of stages of counter current wash can be any amount of stages necessary to produce the water wet carboxylic acid cake to the desired purity. Typically, the amount of stages in the counter current wash can be about 1 to about 8, preferably about 2 to about 6, most preferably about 2 to about 4.

The counter current water wash zone comprises a solid-liquid separation device 120 can typically be comprised of, but not limited to, the following types of devices: centrifuges, cyclones, rotary drum filters, belt filters, press filters, etc. The solid-liquid separation device can be operated within a temperature range of from about 40° C. to about 155° C. Preferably, the second solid-liquid separation device can operate within a temperature range of from about 80° C. to about 150° C. Most preferably, the second solid-liquid separation device can operate within a temperature range of from about 90° C. to about 150° C.

Optionally, the solvent/water byproduct liquor from the counter current water wash zone 120, is segregated from the solvent mother liquor stream produce by the counter current solvent wash zone 80.

Step (d) comprises drying the water-wet carboxylic acid cake 150 in a drying zone 160 to produce a dried carboxylic acid product 170.

The water wet carboxylic acid cake 150 is withdrawn from the counter current water wash zone 120 or the counter current solvent wash zone 80 and fed to the drying zone 160. A portion of the solvent or water and remaining catalyst and impurities is separated, and the dried carboxylic acid cake is withdrawn via line 170.

The drying zone 160 comprises a filter suitable for recovering the solid carboxylic acid and a dryer. The filtration can be accomplished by any means known in the art. For example, a rotary vacuum filter can be used for the filtration to produce a filtration cake. The filtration cake goes through an initial solvent removal step, is then rinsed with acid wash to remove residual catalyst, and can solvent removed again before sent to the dryers. The drying of the filter cake can be accomplished by any means known in the art that's capable of evaporating at least 10% of the volatiles remaining in the filter cake to produce the carboxylic acid product. For example, a Single Shaft Porcupine® Processor dryer can be used.

In other embodiments of this invention step (a), step (b) and step (c) can be combined into one zone known as the liquor exchange zone 250 as shown in FIG. 2. The liquor exchange zone 250 comprises at least one solid-liquid separation device capable of performing the combined function of the solid-liquid separation zone 40, the counter current solvent wash zone 80 and the counter current water wash zone 120 as previously described. Step (b) and step (c) can also be combined into one zone known as the counter current solvent-water liquor exchange zone 260 as shown in FIG. 3. Finally step (a) and step (b) can be combined into one zone known as the solvent liquor exchange zone 270 as show in FIG. 4. In each of the above embodiments comprises at least one solid-liquid separation device capable of performing the functions of the combined zones as previously described. Examples of devices that can be used in the liquor exchange zone 250, or the solvent-water liquor exchange zone 260, or the solvent liquor exchange zone 270 included but are not limited to, the following type of devices centrifuges, cyclones, filters, and such or combination thereof.

We claim:

1. A process for producing a dried carboxylic acid cake, said process comprising:
   (a) oxidizing in an oxidation zone an aromatic feedstock to produce a carboxylic acid slurry;
   (b) removing in a liquor exchange zone impurities from said carboxylic acid slurry to form a water-wet carboxylic acid cake, a mother liquor stream, a solvent mother liquor stream, and a solvent/water byproduct liquor stream; wherein at least one solvent is, added counter current to the flow of said carboxylic acid slurry; wherein said liquor exchange zone comprises one solid-liquid separation device capable of performing the removal of said impurities from said carboxylic acid slurry and producing said water-wet carboxylic acid cake from said carboxylic acid slurry; wherein said solvent comprises acetic acid, and (c) drying said water-wet carboxylic acid cake in a drying zone to form said dried carboxylic acid cake; wherein said water-wet cake maintains the form of a cake between step (b) and (c).

2. The process according to claim 1 wherein said liquor exchange zone comprises from about 2 to about 4 stages of water or solvent counter current washes.

3. The process according to claim 1 wherein said solvent and said water is added counter current to the flow of said carboxylic acid slurry.

4. A process according to claim 1 wherein said carboxylic acid is selected from a group consisting of terephthalic acid, isophthalic acid, naphthalene dicarboxylic acid, trimellitic acid, and mixtures thereof.

5. A process according to claim 1 wherein said carboxylic acid is terephthalic acid.

6. A process according to claim 1, 2 or 3 wherein said drying zone evaporates at least 10% of volatiles in said water-wet carboxylic acid cake.

7. A process according to claim 1 wherein said crude carboxylic acid slurry comprising terephthalic acid, catalyst, acetic acid, and impurities is withdrawn at a temperature between about 110° C. to about 200° C. from said oxidation zone; wherein said catalyst comprises cobalt, manganese and bromine compounds.

8. A process for producing a dried carboxylic acid cake, said process comprising:

(a) oxidizing in an oxidation zone an aromatic feedstock to produce a carboxylic acid slurry;

(b) removing in a solvent liquor exchange zone impurities from said carboxylic acid slurry to form a carboxylic acid cake with solvent, a mother liquor stream, and a solvent mother liquor stream; wherein said solvent comprises acetic acid;

(c) adding water in a counter current water wash zone to said carboxylic cake with solvent to produce a water-wet carboxylic acid cake and a solvent/water byproduct liquor stream; and (d) drying said water-wet carboxylic acid cake in a drying zone to form said dried carboxylic acid cake wherein said water-wet cake maintains the form of a cake between step (c) and (d).

9. A process according to claim 8 wherein said carboxylic acid is selected from a group consisting of terephthalic acid, isophthalic acid, naphthalene dicarboxylic acid, trimellitic acid, and mixtures thereof.

10. A process according to claim 8 wherein said carboxylic acid is terephthalic acid.

11. A process according to claim 8 or 9 wherein said drying zone evaporates at least 10% of volatiles in said water-wet carboxylic acid cake.

12. A process according to claim 8 wherein said crude carboxylic acid slurry comprising terephthalic acid, catalyst, acetic acid, and impurities is withdrawn at a temperature between about 110° C. to about 200° C. from said oxidation zone; wherein said catalyst comprises cobalt, manganese and bromine compounds.

13. A process for producing a dried carboxylic acid cake, said process comprising the following steps in the order named:

(a) oxidizing in an oxidation zone an aromatic feedstock to produce a carboxylic acid slurry;

(b) removing in a solid-liquid separation zone impurities from said carboxylic acid slurry to form a slurry or cake product and a mother liquor stream;

(c) removing in a counter current solvent-water liquor exchange zone impurities from said slurry or cake product to form a water-wet carboxylic acid cake, a solvent mother liquor stream, and a solvent/water byproduct liquor stream; wherein said counter current solvent-water liquor exchange zone comprises one solid-liquid separation device; wherein said solvent comprises acetic acid; and (d) drying said water-wet carboxylic acid cake in a drying zone to form said dried carboxylic acid cake wherein said water-wet cake maintains the form of a cake between step (c) and (d).

14. A process according to claim 13 wherein said carboxylic acid is selected from a group consisting of terephthalic acid, isophthalic acid, naphthalene dicarboxylic acid, trimellitic acid and mixtures thereof.

15. A process according to claim 13 wherein said carboxylic acid is terephthalic acid.

16. A process according to claim 13 wherein said crude carboxylic acid slurry comprising terephthalic acid, catalyst, acetic acid, and impurities is withdrawn at a temperature between about 110° C. to about 200° C. from said oxidation zone; and wherein said catalyst comprises cobalt, manganese and bromine compounds.

17. A process according to claim 13 or 14 wherein said drying zone evaporates at least 10% of volatiles in said water-wet carboxylic acid cake.

18. A process for producing a dried carboxylic acid cake, said process comprising the following steps in the order named:

(a) removing a solvent from a slurry or cake product in a counter current solvent-water liquor exchange zone; wherein a portion of the solvent in said slurry or cake product is replaced with water to form a water-wet carboxylic acid cake; wherein said counter current solvent-water liquor exchange zone comprises one solid-liquid separation device; wherein said solvent comprises acetic acid; and (b) drying said water-wet carboxylic acid cake in a drying zone to form said dried carboxylic acid cake wherein said water-wet cake maintains the form of a cake between step (a) and (b).

19. A process according to claim 18 wherein said carboxylic acid is selected from a group consisting of terephthalic acid, isophthalic acid, naphthalene dicarboxylic acid, trimellitic and mixtures thereof.

20. A process according to claim 18 wherein said carboxylic acid is terephthalic acid.

21. A process according to claim 19 wherein said crude carboxylic acid slurry comprising terephthalic acid, catalyst, acetic acid, and impurities is withdrawn at a temperature between about 110° C. to about 200° C. from said oxidation zone; and wherein said catalyst comprises cobalt, manganese and bromine compounds.

22. A process according to claim 18 or 19 wherein said drying zone evaporates at least 10% of volatiles in said water-wet carboxylic acid cake.

* * * * *